United States Patent
Pozzi et al.

(10) Patent No.: US 7,405,294 B2
(45) Date of Patent: Jul. 29, 2008

(54) INTERMEDIATE CEFDINIR SALTS

(75) Inventors: Giovanni Pozzi, Besana Brianza (IT); Patricio Martin Gomez, Salamaca (ES); Marco Alpegiani, Milan (IT); Walter Cabri, Rozzano (IT)

(73) Assignee: Antibioticos S.p.A., Rodano (IT)

( * ) Notice: Subject to any disclaimer, the term of this patent is extended or adjusted under 35 U.S.C. 154(b) by 0 days.

(21) Appl. No.: 10/529,649

(22) PCT Filed: Sep. 26, 2003

(86) PCT No.: PCT/EP03/10718

§ 371 (c)(1),
(2), (4) Date: Oct. 11, 2005

(87) PCT Pub. No.: WO2004/035800

PCT Pub. Date: Apr. 29, 2004

(65) Prior Publication Data

US 2006/0111566 A1   May 25, 2006

(30) Foreign Application Priority Data

Oct. 1, 2002  (IT) .......................... MI2002A2076

(51) Int. Cl.
*C07D 501/22* (2006.01)
*C07D 501/04* (2006.01)
(52) U.S. Cl. ................................. 540/222
(58) Field of Classification Search .................. 540/222
See application file for complete search history.

(56) References Cited

U.S. PATENT DOCUMENTS

| | | | | |
|---|---|---|---|---|
| 5,114,958 A | * | 5/1992 | Boschelli et al. | 514/361 |
| 6,093,814 A | * | 7/2000 | Lee et al. | 540/222 |
| 6,153,645 A | * | 11/2000 | Finn et al. | 514/468 |
| 6,319,955 B1 | * | 11/2001 | Alessandrini et al. | 514/665 |
| 6,346,583 B1 | * | 2/2002 | Kilgour et al. | 525/474 |
| 7,071,329 B2 | * | 7/2006 | Monguzzi et al. | 540/226 |
| 7,244,842 B2 | * | 7/2007 | Desphande et al. | 540/222 |
| 2003/0225007 A1 | * | 12/2003 | Tam et al. | 514/42 |
| 2004/0019198 A1 | * | 1/2004 | Crich et al. | 536/55.3 |
| 2005/0203006 A1 | * | 9/2005 | Hill et al. | 514/9 |
| 2006/0094703 A1 | * | 5/2006 | Deshpande et al. | 514/202 |
| 2006/0149056 A1 | * | 7/2006 | Singh et al. | 540/222 |
| 2008/0033169 A1 | * | 2/2008 | Pozzi et al. | 544/54 |

FOREIGN PATENT DOCUMENTS

| | | | |
|---|---|---|---|
| EP | 1273587 A1 | * | 1/2003 |
| WO | WO 97/24358 A1 | | 7/1997 |
| WO | WO 98/45299 A | | 10/1998 |
| WO | WO 02/098884 A1 | | 12/2002 |
| WO | WO 2004056835 A1 | * | 7/2004 |
| WO | WO 2006006040 A2 | * | 1/2006 |

OTHER PUBLICATIONS

McGraw-Hill Dictionary of Chemistry, Mcgraw-Hill, International Edition (1986), p. 14.*
Condensed Chemical Dictionary, Reinhold, Seventh Edition (1966), apge 19.*
Wikipedia entry for "Acyl" <http://en.wikipedia.org/wiki/Acyl>.*
WordNet entry for Acyl <http://wordnet.princeton.edu/perl/webwn2.1>.*
"acyl groups" (IUPAC Compendium of Chemical Terminology 2nd Edition (1997)) <http://www.iupac.org/goldbook/A00123.pdf> Downloaded from the internet Mar. 26, 2007.*
Reference "acyl group" (Datasegment.com), <http://onlinedictionary.datasegment.com/word/acyl+group> Downloaded from the internet Mar. 26, 2007.*
"acyl" (Academic Press Dictionary of Science and Technology) <http://www.xreferplus.com/entry/3067635> Downloaded from the internet Mar. 26, 2007.*
The Friedel-Crafts Acylation of Benzene <http://www.chemguide.co.uk/mechanisms/elsub/fcacyl.html> Downloaded from the internet Mar. 26, 2007.*
Okamoto et al., "*Degradation Kinetics and Isomerization of Cefdinir, A New Oral Cephalosporin, in Aqueous Solution*", Journal of Pharmaceutical Sciences, Sep. 1996, pp. 976-983, vol. 85 (9).

* cited by examiner

*Primary Examiner*—Mark L Berch
(74) *Attorney, Agent, or Firm*—Rothwell, Figg, Ernst & Manbeck, P.C.

(57) ABSTRACT

Disclosed are salts of the general formula (I)

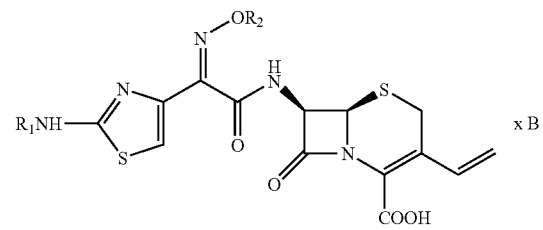

wherein $R_1$, $R_2$ and B are defined in the description. These salts are useful intermediates for the preparation of cefdinir. Also, disclosed are processes for the preparation thereof from the compounds of the general formula (II) and (III).

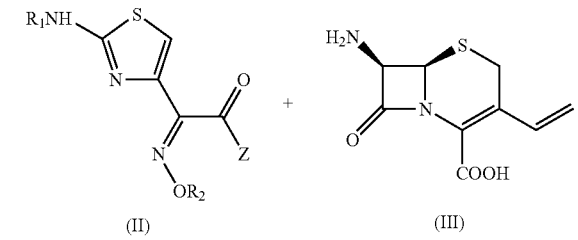

Further, disclosed is a method of producing cefdinir from the salts of the general formula (I) including the steps of removing protecting groups.

17 Claims, No Drawings

INTERMEDIATE CEFDINIR SALTS

CROSS REFERENCE TO RELATED APPLICATION

This application is a 35 USC § 371 National Phase Entry Application from PCT/EP2003/010718, filed Sep. 26, 2003, and designating the United States.

FIELD OF THE INVENTION

The present invention relates to cephalosporins, in particular to cefdinir intermediates and to a process for the preparation of said intermediates.

SUMMARY

The present invention relates to salts of general formula (I)

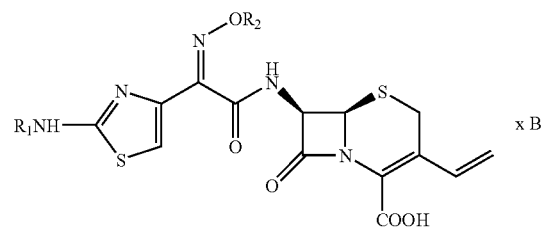

(I)

x B wherein $R_1$, $R_2$ and B are as defined in the description. These salts are useful as intermediates for the preparation of cefdinir.

Compounds (I) can be obtained through a process comprising the reaction of a compound of formula (II)

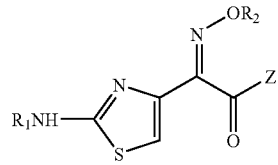

(II)

wherein $R_1$ and $R_2$ are as defined in the description, with 7-amino-3-vinyl-3-cephem-4-carboxylic acid of formula (III)

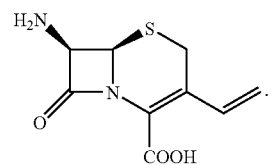

(III)

BACKGROUND OF THE INVENTION

[(−)-(6R,7R)]-7-((Z)-2-(2-Amino-4-thiazol)-2-hydroxy-iminoacetamido)-8-oxo-3-vinyl-5-thia-1-azabicyclo[4.2.0]-oct-2-ene-2-carboxlic acid (IV), commonly known as cefdinir,

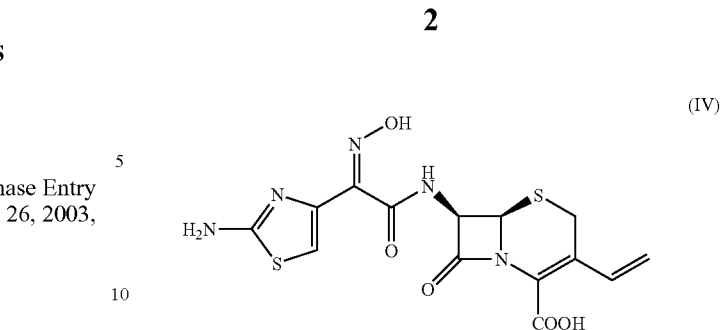

(IV)

is a third generation semisynthetic cephalosporin for oral use, characterized by a broad antibacterial spectrum against gram-positive and gram-negative bacteria, its antibiotic activity being higher than that of other antibiotics for oral administration. In particular, it shows excellent antibacterial activity against staphylococci and streptococci.

Cefdinir is usually synthesized through intermediates of formula (V) wherein the hydroxyimino group (and optionally the primary amino group) is protected

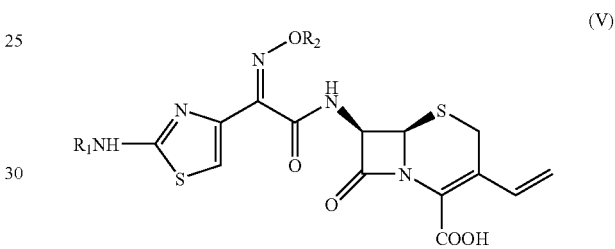

(V)

$R_1$ and $R_2$ being as defined in the description.

According to the literature, the intermediates (V) can be obtained in different ways, but their recovery is troublesome and not convenient from the industrial standpoint.

For example, according to WO 97/24358, an intermediate of formula (V) wherein $R_1$ is hydrogen and $R_2$ is trityl (Va), is recovered as the salt with p-toluenesulfonic acid (VIa)

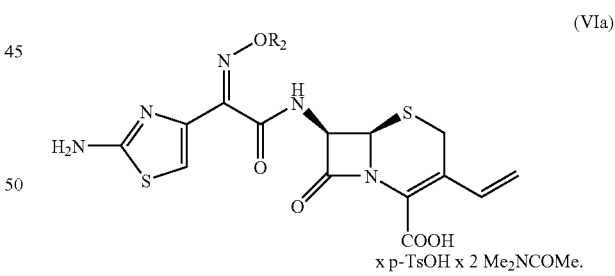

(VIa)

x p-TsOH x 2 Me$_2$NCOMe.

The drawback of this method is that the recovery is accomplished by adding to the reaction mixture anti-solvents such as ethers, which are dangerous and therefore not suitable for industrial use.

Other methods do not envisage recovery of the intermediates (V); as a consequence, the quality of the final product is poor and further purifications are required (WO 98/45299; Kamachi, H. et al., *J. Antibiot.* 1988 41(11), 1602-16).

Alternatively, the side chain can be linked to the cephalosporanic nucleus by means of subsequent synthetic steps, with decrease in the overall yield and increase in the process time (U.S. Pat. No. 4,559,334, EP 304019).

The intermediates (V) can also be recovered from water as free acids, but filtration and drying are very difficult.

DETAILED DESCRIPTION OF THE INVENTION

It has now been found that the intermediates (V) can be recovered in high yield and purity as the salts with ammonia or organic bases, in inert organic solvents of common industrial use, thus remarkably improving the manufacture of cefdinir in terms of time, costs and quality of the end product.

Accordingly, the present invention relates to salts of formula (I)

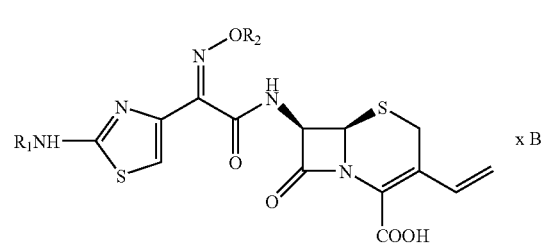

(I)

wherein $R_1$ is hydrogen or an amino-protecting group, for example a $C_1$-$C_6$ acyl group optionally substituted with one or more fluorine or chlorine atoms, preferably formyl, an alkyl- or aryl-oxycarbonyl group, preferably tert-butoxycarbonyl and p-methoxybenzyloxycarbonyl, or a trityl group wherein each benzene ring is optionally substituted with one or more methoxy and/or methyl groups, preferably trityl;

$R_2$ is a hydroxy-protecting group, for example a straight or branched $C_1$-$C_6$ alkyl group, preferably tert-butyl, a benzyl, benzhydryl or trityl group wherein each benzene ring is optionally substituted with one or more methoxy, nitro and/or methyl group, preferably p-methoxybenzyl, 3,4-dimethoxybenzyl, benzhydryl, bis(p-methoxyphenyl)methyl and trityl;

B is ammonia or an organic base selected from primary amines, preferably cyclohexylamine, 2-ethylhexylamine, benzylamine, α-methylbenzylamine and tert-octylamine; secondary amines, preferably diethylamine, morpholine, dicyclohexylamine, N,N-methylbenzylamine or N,N'-dibenzylethylenediamine; tertiary amines, preferably triethylamine, tributylamine, triisooctylamine, ethyldiisopropylamine, N-methylmorpholine, pyridine, 2,6-lutidine or quinoline; guanidine, preferably 1,1,3,3-tetramethylguanidine; amidines, preferably 1,5-diazabicyclo[4.3.0]non-5-ene (DBN) or 1,8-diazabicyclo[5.4.0]undec-7-ene (DBU); hydrates, solvates or adducts thereof.

A preferred salt according to the invention is the dicyclohexylamine salt of the formula (Ia)

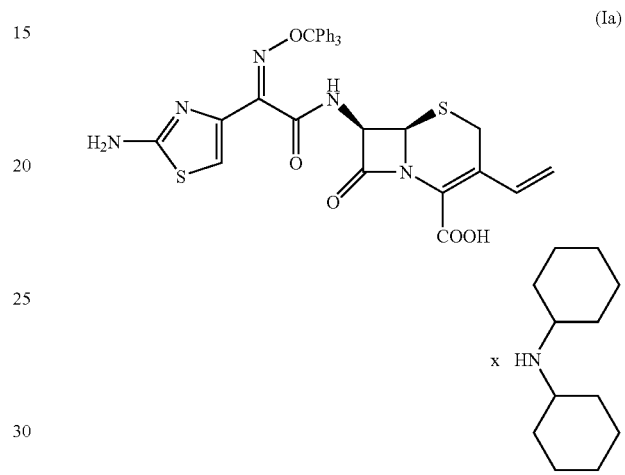

(Ia)

The salts of formula (I) are obtained through a process which envisages three possible alternatives, whose common feature is that the acids of the formula (V) are not isolated. The alternatives are illustrated in the following scheme.

Scheme

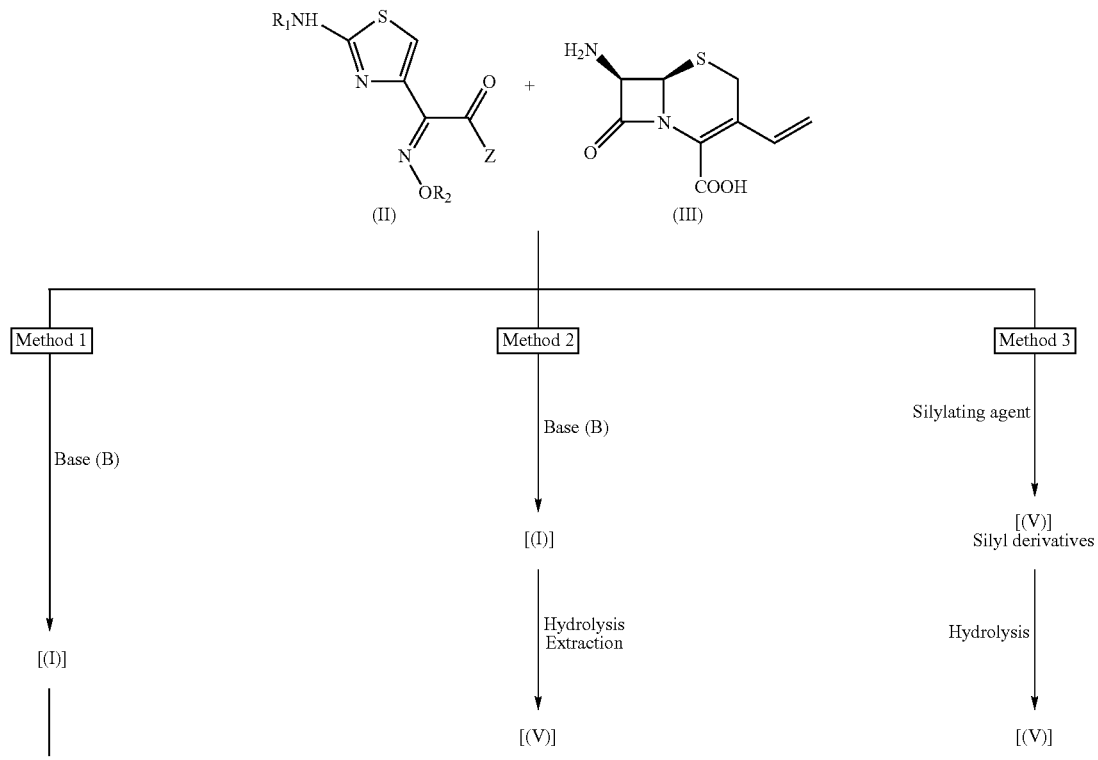

-continued

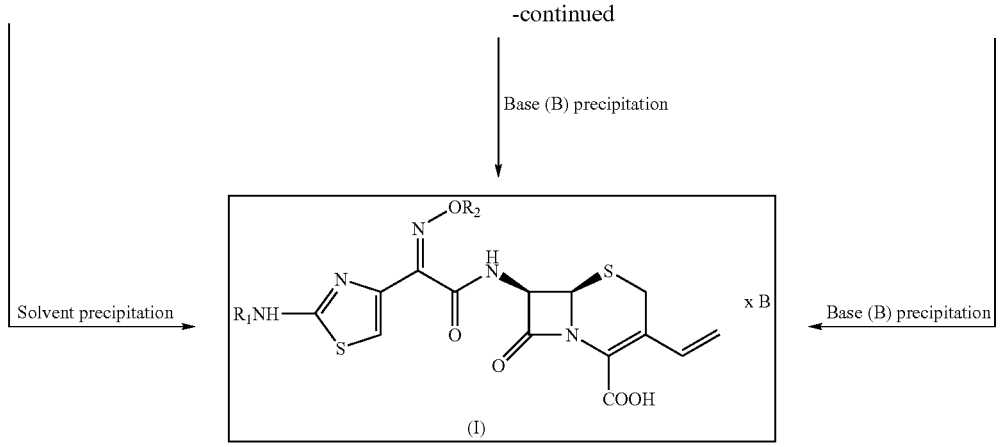

In a first embodiment of the invention (method 1), an activated 2-(aminothiazol-4-yl)-2-(hydroxyimino)acetic acid derivative of formula (II)

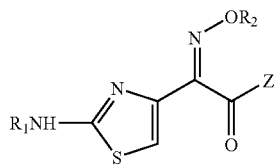

wherein $R_1$ and $R_2$ are as defined above and Z is a carboxy-activating group selected from —Cl, —S-mercaptobenzothiazolyl, —O—P$^+$(Ph)$_3$Cl$^{31}$, —O—P(S)(OEt)$_2$, —O—P(O)(OEt)$_2$, —O—SO$_2$Me, —O—SO$_2$Ph, —O—SO$_2$-pTol, —O—COtBu, —O—C(O)OEt, —O-benzotriazol-1-yl, —S-(2-methyl-thiadiazol-5-yl), —O—CH=N$^+$(CH$_3$)$_2$Cl$^{31}$ or benzotriazol-1-yl-3-oxide, is reacted with 7-amino-3-vinyl-3-cephem-4-carboxylic acid (III),

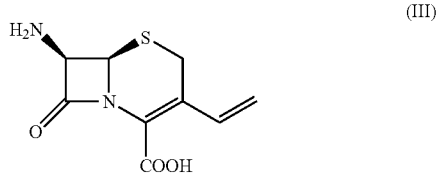

in the presence of ammonia or an organic base selected from those listed above. The compounds (II) and (III) comprise also their hydrates and solvates. The reaction is carried out in an organic solvent selected from: halogenated hydrocarbons, preferably methylene chloride; carboxylic acid esters, preferably dimethylcarbonate, ethyl acetate and butyl acetate; ketones, preferably acetone, methyl ethyl ketone and methyl isobutyl ketone; nitriles, preferably acetonitrile or propionitrile; amides, preferably N,N-dimethylformamide, N,N-dimethylacetamide, N-methylpyrrolidone; aromatic hydrocarbons, preferably toluene and xylene; ethers, preferably tetrahydrofuran, dioxane or ethylene glycol dimethyl ether; sulfoxides or sulfones, preferably dimethylsulfoxide, dimethyl sulfone and sulfolane; alcohols, preferably methanol or ethanol, or mixtures thereof, optionally in the presence of water, at a temperature ranging from −20° C. to +80° C., preferably from 0° C. to 40° C. Preferred solvents according to the invention are N,N-dimethylformamide and N,N-dimethylacetamide. The amount of base can be stoichiometric to the compound of formula (III) or in molar excess up to 3 times, preferably ranging from 1 to 2 equivalents.

The resulting salts of the formula (I) precipitate by addition of an anti-solvent selected from those listed above. The crystallization temperature may range from −20° C. to 50° C., preferably from −10° C. to 30° C.

In a second embodiment of the invention (method 2) the reaction is carried out as described above, but the salts (I) are not immediately precipitated, rather converted to an acid of the formula (V), which is extracted from the reaction mixture and precipitated from the extraction solvent by treatment with ammonia or an amine selected from those listed above, which can be the same or different from that used in the previous step. The salt is precipitated using an amount of base stoichiometric to the acid of the formula (V) or in molar excess up to two times, preferably ranging from 1 to 1,5 equivalents. Also in this case the crystallization temperature may range from −20° C. to 50° C., preferably from −10° C. to 30° C. According to a preferred embodiment of this method, compounds (II) and (III) are reacted with 1,1,3,3-tetramethylguanidine or triethylamine. Preferably, the compound of formula (II) is the S-mercaptobenzothiazolyl thioester (IIa)

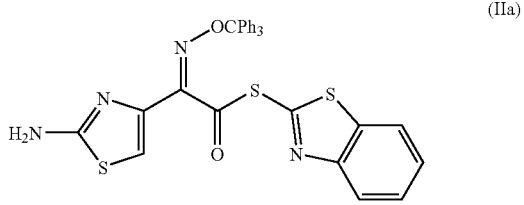

and the compound of formula (III) is 7-amino-3-vinyl-3-cephem-4-carboxylic acid (III)

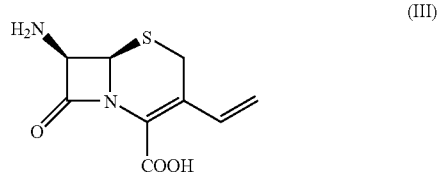

In a third embodiment of the invention (method 3), the reaction between the compounds (II) and (III) is carried out in the presence of a silylating agent, preferably N,O-bis-trimethylsilylacetamide. The acid of formula (V) obtained after hydrolysis is extracted and precipitated as a salt of formula (I) by treatment with ammonia or with an amine selected from those listed above. Also in this case, use will be made of an amount of base stoichiometric to the acid of formula (V) or in molar excess up to two times, preferably ranging from 1 to 1,5 equivalents. According to a preferred embodiment of this method, the ester (IIa) is reacted with the acid (IIIa) in the presence of N,O-bis-trimethylsilylacetamide, to give, after hydrolysis, the acid (Va)

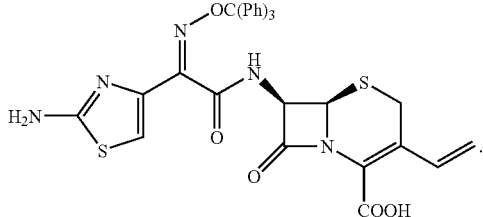

(Va)

Among the three methods disclosed above, the second and the third ones are particularly preferred, as they allow to obtain the salts of formula (I) with higher purity.

The salts (I) precipitate as crystals from the reaction mixture and can be easily recovered by filtration or centrifugation. Through crystallization of the salts (I), the intermediates (V) are removed off the reaction medium; degradation is thus remarkably reduced, while the yield and quality of the intermediates are increased. The salts (I) can be obtained in the anhydrous form, or as hydrates, or can also be recovered as solvates. Hydration water or solvation solvent can be sometimes removed in part or almost completely by drying under reduced pressure, which increases the stability of the product. Typically, a salt having a water content of 0.5% or lower and a solvent content of 3% or lower can be obtained after drying. The salts of formula (I) can also be recovered as adducts with derivatives of formula H-Z, wherein Z is as defined above. The derivatives of formula H-Z can be present in a molar ratio of 1:1 or lower.

The conversion of the salts (I) to cefdinir (IV) by removal of the protecting groups can be carried out according to methods already known in the literature (WO 0179211, WO 9724358, Kamachi, H. et al., *J. Antibiot.* 1988 41(11), 1602-16).

The following examples illustrate the invention in greater detail.

EXAMPLES

Example 1

Preparation of 7-[2-(aminothiazol-4-yl)-2-(trityloxyimino)-acetamido]-3-vinyl-3-cephem-4-carboxylic acid dicyclohexylamine salt 1,1,3,3-Tetramethylguanidine (35.8 ml) is added in 15 min to a suspension of 7-amino-3-vinyl-3-cephem-4-carboxylic acid (65.0 g) in N,N-dimethylformamide (0.78 L) previously cooled to 10° C. and the mixture is stirred at this temperature until complete dissolution. 2-(Aminothiazol-4-yl)-2-(trityloxyimino)acetic acid S-mercaptobenzothiazolic ester (172.7 g) is added thereto in 15 min and the mixture is stirred at this temperature until complete conversion of 7-amino-3-vinyl-3-cephem-4-carboxylic acid (HPLC analysis). After completion of the reaction, water (1.7 L) and ethyl acetate (2.2 L) are added and the pH is adjusted to 3.0 with diluted hydrochloric acid. The phases are separated and the organic one is washed with a 20% sodium chloride solution in water (0.86 L). The phases are separated and dicyclohexylamine (54.1 ml) is added in 30 min to the organic one. Formation of crystals is observed. After further 15 min the mixture is cooled to 0° C., stirred at this temperature for 1 hour, thereafter the precipitate is filtered, washed with ethyl acetate (1.7 L) and dried. 226.0 g of the title compound are obtained.

$^1$H-NMR (DMSO-$d_6$, 300 MHz): 9.86 (1H, d, J=8.3 Hz, —CONH—), 7.34-7.20 (15H, m, Ph$_3$), 7.01 (1H, dd, J=17.9 e 11.6 Hz, —CH═CH$_2$), 6.59 (1H, s, H-heteroaryl), 5.78 (1H, dd, J=8.3 and 5.0 Hz, —CONH—CH—), 5.24 (1H, d, J=17.9 Hz, —CH═CHH trans), 5.15 (1H, d, J=5.0 Hz, —CON—CH—), 5.00 (1H, d, J=11.6 Hz, —CH═CHH cis), 3.61 (1H, AB system, $J_{AB}$=17.0 Hz, —SCH$_2$), 3,46 (1H, AB system, $J_{AB}$=17.0 Hz, —SCH$_2$), 3.06–3.00 (2H, m, 2×HN—CH dicyclohexylamine), 1.99-1.06 (20H, m, 10×CH$_2$ dicyclohexylamine).

Example 2

Preparation of 7-[2-(aminothiazol-4-yl)-2-(trityloxyimino)-acetamido]-3-vinyl-3-cephem-4-carboxylic acid dicyclohexylamine salt Triethylamine (9.1 ml) is added in 20 min to a suspension of 7-amino-3-vinyl-3-cephem-4-carboxylic acid (7.5 g) in N,N-dimethylformamide (90 ml) previously cooled to 15° C. 2-(Aminothiazol-4-yl)-2-(trityloxyimino)acetic acid S-mercaptobenzothiazolic ester (19.7 g) is added thereto in 15 min and the mixture is stirred at this temperature until complete conversion of 7-amino-3-vinyl-3-cephem-4-carboxylic acid (HPLC analysis). After completion of the reaction water (200 ml) and ethyl acetate (250 ml) are added and the pH is adjusted to 3.0 with diluted hydrochloric acid. The phases are separated and the organic one is washed with a 20% sodium chloride solution in water (200 ml). The phases are separated and dicyclohexylamine (7.2 ml) is added to the organic one in 15 min. Formation of crystals is observed. After further 15 min the mixture is cooled to 0° C., stirred at this temperature for 1 hour, thereafter the precipitate is filtered, washed with ethyl acetate (100 ml) and dried. 26.4 g of the title compound are obtained.

Example 3

Preparation of 7-[2-(aminothiazol-4-yl)-2-(trityloxyimino)-acetamido]-3-vinyl -3-cephem-4-carboxylic acid dicyclohexylamine salt N,O-bistrimethylsilylacetamide (8.0 ml) is added in 15 min to a suspension of 7-amino-3-vinyl-3-cephem-4-carboxylic acid (7.5 g) in N,N-dimethylacetamide (50 ml) at 25° C. After further 20 min, 2-(aminothiazol-4-yl)-2-(trityloxyimino)acetic acid S-mercaptobenzothiazolic ester (19.8 g) is added and the mixture is stirred at this temperature until complete conversion of 7-amino-3-vinyl-3-cephem-4-carboxylic acid (HPLC analysis). After completion of the reaction, ethyl acetate (250 ml) and methanol (3 ml) are added and the mixture is stirred for 15 minutes. Water is then added (200 ml) and stirring is continued for further 15 min.

The phases are separated and the organic one is washed with a 20% sodium chloride solution in water (200 ml). The phases are separated and dicyclohexylamine (7.2 ml) is added to the organic phase in 15 min. Formation of crystals is observed. The mixture is allowed to stand for further 15 min, cooled to 0° C. and stirred at this temperature for 1 hour. The precipitate is filtered, washed with ethyl acetate (100 ml) and dried. 25.8 g of the title compound are obtained.

Example 4

Preparation of 7-[2-(aminothiazol-4-yl)-2-(trityloxy-imino)-acetamido]-3-vinyl-3-cephem-4-carboxylic acid (R)-(+)-α-methylbenzylamine salt The same procedure as example 3 is initially followed. After washing the organic phase with aqueous sodium chloride, (R)-(+)-α-methylbenzylamine (4.6 ml) is added in 15 minutes. Formation of crystals is observed. The mixture is allowed to stand for further 15 min, cooled to 0° C. and stirred at this temperature for 1 hour. The precipitate is filtered, washed with ethyl acetate (100 ml) and dried. 20.4 g of the title compound are obtained.

$^1$H-NMR (DMSO-d$_6$, 300 MHz): 9.84 (1H, d, J=8.0 Hz, —CONH—), 7.49-7.18 (20H, m, 4×Ph), 7.01 (1H, dd, J=17.6 and 11.0 Hz, —CH═CH$_2$), 6.59 (1H, s, H-heteroaryl), 5.77 (1H, dd, J=8.0 and 5.0 Hz, —CONH—CH—), 5.20 (1H, d, J=17.6 Hz, —CH═CHH trans), 5.13 (1H, d, J=5.0 Hz, —CON—CH—), 4.97 (1H, d, J=11.6 Hz, —CH═CHH cis), 4.34 (1H, q, J=6.9 Hz, CHMe benzylamine), 3.58 (1H, AB system, $J_{AB}$=17.1 Hz, —SCH$_2$), 3.45 (1H, AB system, $J_{AB}$=17.1 Hz, —SCH$_2$), 1.47 (3H, d, J=6.9 Hz, Me).

The invention claimed is:

1. An isolated salt as set forth in formula (I)

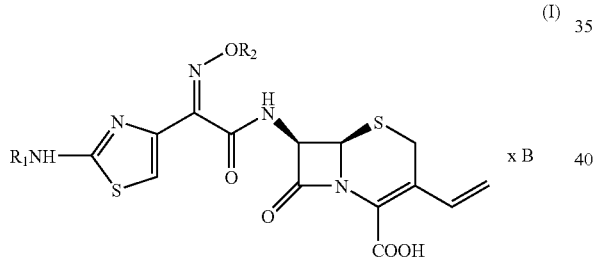

(I)

wherein
R$_1$ is hydrogen or an amino-protecting group, selected from formyl, an alkyl- or aryl-oxycarbonyl group, or a trityl group wherein each benzene ring is optionally substituted with one or more methoxy and/or methyl groups:
R$_2$ is a hydroxy-protecting group selected from a straight or branched C$_1$-C$_6$ alkyl group, a benzyl, benzhydryl or trityl group wherein each benzene ring is optionally substituted with one or more methoxy, nitro and/or methyl groups;
B is ammonia or an organic base selected from primary amines, secondary amines, tertiary amines, guanidine, amidines or an adduct thereof, wherein said adduct is a complex of said salt and a compound represented as H-Z, wherein H is hydrogen; and
Z is selected from, —S-mercaptobenzothiazolyl, —O—P$^+$(Ph)$_3$Cl$^-$, —O—C(O)OEt, —O-benzotriazol-1-yl, —S-(2-methyl-thiadiazol-5-yl) and —O—CH═N$^+$(CH$_3$)$_2$Cl$^-$ or benzotriazol-1-yl-3-oxide; and
wherein the salt is isolated from a reaction medium.

2. The salt as claimed in claim 1 wherein R$_1$ is a tert-butoxycarbonyl, p-methoxybenzyloxycarbonyl, or trityl group.

3. The salt as claimed in claim 1 wherein R$_2$ is a tert-butyl, p-methoxybenzyl, 3,4-dimethoxybenzyl, benzhydryl, bis(p-methoxyphenyl)methyl or trityl group.

4. The salt as claimed in claim 1 wherein R$_1$ is hydrogen and R$_2$ is trityl.

5. The salt as claimed in claim 1 in which B is a primary amine selected from cyclohexylamine, 2-ethylhexylamine, benzylamine, α-methylbenzylamine and tert-octylamine.

6. The salt as claimed in claim 1 in which B is a secondary amine selected from diethylamine, morpholine, dicyclohexylamine, N,N-methylbenzylamine or N, N$^1$-dibenzylethylenediamine.

7. The salt as claimed in claim 6 wherein B is dicyclohexylamine.

8. The salt as claimed in claim 1 wherein B is a tertiary amine selected from triethylamine, tributylamine, triisooctylamine, ethyldiisopropylamine, N-methylmorpholine, pyridine, 2,6-lutidine or quinoline.

9. The salt as claimed in claim 1 wherein B is 1,1,3,3-tetramethylguanidine.

10. The salt as claimed in claim 1 wherein B is 1,5-diazabicylclo[4.3.0]non-5-ene (DBN) or 1,8-diazabicyclo[5.4.0]undec-7-ene(DBU).

11. A salt as set forth in formula (I)

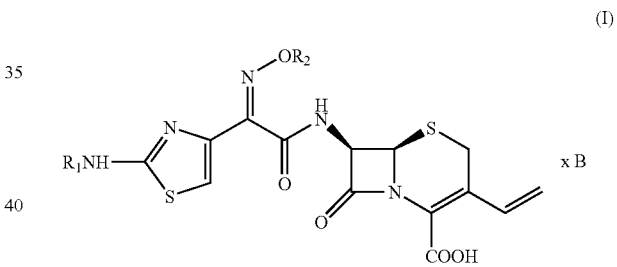

(I)

wherein
R$_1$ is R$_1$ is a formyl, tert-butoxycarbonyl, p-methoxybenzyloxycarbonyl, or trityl group:
R$_2$ is a hydroxy-protecting group selected from a straight or branched C$_1$-C$_6$ alkyl group, a benzyl, benzhydryl or trityl group wherein each benzene ring is optionally substituted with one or more methoxy, nitro and/or methyl groups;
B is ammonia or an organic base selected from primary amines, secondary amines, tertiary amines, guanidine, amidines or an adduct thereof, wherein said adduct is a complex of said salt and a compound represented as H-Z, wherein H is hydrogen; and
Z is selected from, —S-mercaptobenzothiazolyl, —O—P$^+$(Ph)$_3$Cl$^-$, —O—(O)OEt, —O—benzotriazol-1-yl, —S-(2-methyl-thiadiazol-5-yl) and —O—CH═N$^+$(CH$_3$)$_2$Cl$^-$ or benzotriazol-1-yl-3-oxide.

12. A method of synthesizing a salt of cefdinir, comprising the step of deprotecting the salt of claim 1.

13. The salt of claim 11, wherein said salt is set forth in formula (Ia)

(Ia)

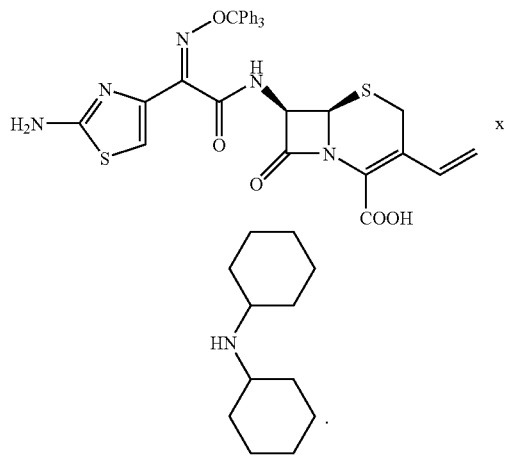

14. A method of synthesizing a salt of cefdinir, comprising the step of deprotecting the salt of claim 11.

15. A salt as set forth in formula (I)

(I)

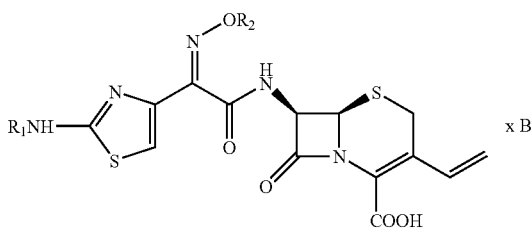

wherein
R₁ is an amino-protecting group, selected from an alkyl- or aryl-oxycarbonyl group, or a trityl group wherein each benzene ring is optionally substituted with one or more methoxy and/or methyl groups;

R₂ is a hydroxy-protecting group selected from a straight or branched $C_1$-$C_6$ alkyl group, a benzyl, benzhydryl or trityl group wherein each benzene ring is optionally substituted with one or more methoxy, nitro and/or methyl groups; and B is ammonia or an organic base selected from primary amines, secondary amines, tertiary amines, guanidine, amidines or an adduct thereof, wherein said adduct is a complex of said salt and a compound represented as H-Z, wherein H is hydrogen; and Z is selected from —S-mercaptobenzothiazolyl, —O—P⁺(Ph)₃Cl³¹, —O—C(O)OEt, —O-benzotriazol-1-yl, —S-(2-methyl-thiadiazol-5-yl) and —O—CH=N⁺(CH₃)₂Cl⁻ or benzotriazol-1-yl-3-oxide.

16. An adduct of a salt of claim 15.

17. A crystal of a salt as set forth in formula (I)

(I)

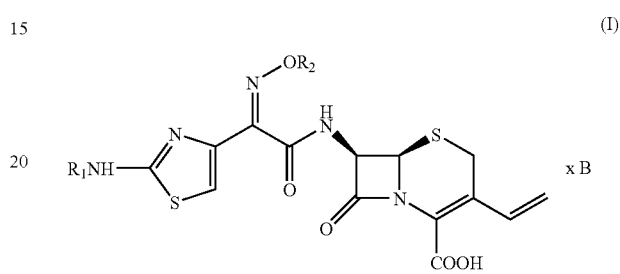

wherein
R₁ is hydrogen or an amino-protecting group, selected from formyl, an alkyl- or aryl-oxycarbonyl group, or a trityl group wherein each benzene ring is optionally substituted with one or more methoxy and/or methyl groups:

R₂ is a hydroxy-protecting group selected from a straight or branched $C_1$-$C_6$ alkyl group, a benzyl, benzhydryl or trityl group wherein each benzene ring is optionally substituted with one or more methoxy, nitro and/or methyl groups;

B is ammonia or an organic base selected from primary amines, secondary amines, tertiary amines, guanidine, amidines or an adduct thereof, wherein said adduct is a complex of said salt and a compound represented as H-Z, wherein H is hydrogen; and Z is selected from —S-mercaptobenzothiazolyl, —O—P⁺(Ph)₃Cl³¹, —O—C(O)OEt, —O-benzotriazol-1-yl, —S-(2-methyl-thiadiazol-5-yl) and —O—CH=N⁺(CH₃)₂Cl⁻ or benzotriazol-1-yl-3-oxide.

* * * * *